US00PP14729P3

(12) United States Plant Patent
Murakami

(10) Patent No.: US PP14,729 P3
(45) Date of Patent: Apr. 20, 2004

(54) PETUNIA PLANT NAMED 'SUNBELRIKUPI'

(50) Latin Name: *Petunia hybrida*
Varietal Denomination: Sunbelrikupi

(75) Inventor: Yasuyuki Murakami, Gamo-gun (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/327,017

(22) Filed: Dec. 24, 2002

(65) Prior Publication Data

US 2003/0126664 P1 Jul. 3, 2003

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

Disclosed herein is a new and distinct variety of Petunia plant having a decumbent growth habit. The Petunia plant has abundant branching particularly with respect to secondary branching, and great profusion of blooms with the entire plant remaining in bloom for a considerable period of time. The flowers are single and small with the petals having a vivid reddish-purple color. The base color of the corolla throat is brilliant greenish-yellow. The outside color of the corolla throat is light greenish-yellow. The plant exhibits high resistance to rain, heat, drought and diseases such as powdery mildew.

2 Drawing Sheets

Botanical/commercial classification: *Petunia hybrida*/Petunia Plant.
Varietal denomination: *cv. 'Sunbelrikupi'*.

BACKGROUND OF THE VARIETY

The Petunia is a very popular plant that is used for flower bedding and potting in the summer season. There are only a few small-flowered petunias, such as, 'Suntory SP-R' (U.S. Plant Pat. No. 9,577, 'Sunberubu' (U.S. Plant Pat. No. 9,754), 'Sunbelchipi' (U.S. Plant Pat. No. 10,355) and 'Sunbeluki' (U.S. Plant Pat. No. 11,558). These Petunias are of the semi-decumbent type and have a medium plant height, abundant branching, and a high resistance to heat, rain and disease. However there are only a few varieties having a decumbent habit, a great profusion of flowers, a vivid reddish-purple flower color, a very small flower size, and a high resistance to rain, heat, cold and disease. Accordingly, this invention is aimed at obtaining a new variety having vivid reddish-purple petals, and very small flowers combined with the above features.

The new variety of Petunia plant according to this invention originated from crossing of 'Sunbelchipi' variety as female parent (U.S. Plant Pat. No. 10,355) and the 'Sunbelkupi' variety as male parent (U.S. Plant Pat. No. 10,287).

The crossing was conducted in May 1996 at the Oumi R&D Center of SUNTORY Ltd., located at 863-1, Aza-Iketani, Omori-cho, Youkaichi-shi, Shiga-ken, Japan. From this crossing 50 seedlings were obtained and five seedlings were selected in view of their semi-erect growth habit and vivid reddish-purple colored petals at the end of September 1997. These five seedlings were grown and were tested and evaluated during potting and bedding trials. Only one plant of the present invention was selected in September 1998. The selected plant was propagated by the use of cuttings and then was grown in pots in a greenhouse trial and in the field at the Omi R&D Center from April to November 1999. The botanical characteristics of the finally selected plant were examined using the similar 'Sunbelkupi' variety (U.S. Plant Pat. No. 10,287), for comparison. As a result, it was concluded that this new Petunia plant is distinguishable from any other variety whose existence is known to me and is uniform and stable in its characteristics. This new variety of Petunia plant was named 'Sunbelrikupi'.

The new variety of the present invention can be readily distinguished from the 'Sunbelros' variety (U.S. Plant patent application Ser. No. 10/326,967, filed Dec. 24, 2002) and the 'Sunbelre' variety (U.S. Plant patent application Ser. No. 10/327,030, filed Dec. 24, 2002) through an observation of the flower coloration. Each of these varieties had the same female parent. The new 'Sunbelrikupi' variety of the present invention forms vivid reddish-purple flowers, the 'Sunbelros' variety forms deep purplish-pink flowers, and the 'Sunbelre' variety forms deep red flowers.

In the following description, the color information is in accordance with The R.H.S. Colour Chart of The Royal Horticultural Society, London, England. A color chart based on The Japan Color Standard for Horticultural Plants (J.H.S. Color Chart) is also added for reference.

The main botanical characteristics of the 'Sunbelchipi' female parent variety are as follows:

Plant:
- *Growth habit.*—Semi-decumbent.
- *Plant height.*—Approximately 15–16 cm.
- *Spreading area of plant.*—The stem extends to a length of approximately 11–13 cm from the base.
- *Blooming period.*—April to late October in the southern Kanto area, Japan. The plant shape does not change throughout this period.

Stem:
- *Thickness.*—Approximately 2.3 mm.
- *Pubescence.*—Present.
- *Branching.*—Abundant with the superior branching propensity, especially secondary branches.
- *Length of internode.*—Approximately 1.4 cm.

Leaf:
- *Shape.*—Lanceolate.
- *Length.*—Approximately 5.1 cm.
- *Width.*—Approximately 1.6 cm.
- *Color.*—Dark yellow-green (R.H.S. 146A, J.H.S. 3508).
- *Thickness.*—Approximately 0.2–0.4 mm.
- *Pubescence.*—Sparse.
- *Leaf attachment angle to stem.*—Slanted upward to horizontal.

Flower:
- *Facing direction.*—Horizontal.
- *Type.*—Single.
- *Shape.*—Funnel-shaped, with five fissures.
- *Shape of petal tip.*—Round.
- *Waviness of petal.*—Weak.
- *Lobation of petal.*—Shallow.
- *Diameter.*—Approximately 2.8–2.9 cm.
- *Color.*—Petal: Vivid reddish-purple (R.H.S. 57C, J.H.S. 9707). Base color of corolla throat: Strong yellow (R.H.S. 9A, J.H.S. 2513). Outside color of corolla tube: Light greenish-yellow (R.H.S. 5C, J.H.S. 2904).
- *Reproductive organs.*—1 normal pistil and 5 normal stamens.
- *Fertility.*—Fertile, but self-incompatible.
- *Peduncle.*—Approximately 0.7–0.8 mm in thickness, and approximately 1.9 cm in length.
- *Physiological and ecological characteristics.*—High resistance to heat, rain, drought and diseases, such as powdery mildew. The resistance to heat and rain is very strong.
- *Blooming.*—A bloom commonly lasts approximately 10 days on the plant. Pinching is not necessary to ensure continuous blooming; however, it does tend to enhance bloom production.

The main botanical characteristics of the 'Sunbelkupi' male parent are as follows:

Plant:
- *Growth habit.*—Decumbent.
- *Plant height.*—Approximately 5.8–6.1 cm.
- *Spreading area of plant.*—The stem extends to a length of approximately 18–19 cm from the base.
- *Blooming period.*—April to late October in the southern Kanto area, Japan. The plant shape does not change throughout this period.

Stem:
- *Thickness.*—Approximately 1.2 mm.
- *Pubescence.*—Sparse.
- *Branching.*—Very abundant with a superior branching propensity, especially secondary branches.
- *Length of internode.*—Approximately 1.3 cm.

Leaf:
- *Shape.*—Lanceolate.
- *Length.*—Approximately 3.5 cm.
- *Width.*—Approximately 1.0 cm.
- *Thickness.*—Approximately 0.2–0.3 mm.
- *Pubescence.*—Sparse.
- *Color.*—Dark green (R.H.S. 137B, J.H.S. 3707).
- *Leaf attachment angle to stem.*—Slanted upward to horizontal.

Flower:
- *Facing direction.*—Slanted upward to horizontal.
- *Type.*—Single.
- *Shape.*—Funnel-shaped, with five fissures.
- *Shape of petal tip.*—Round.
- *Waviness of petal.*—Weak.
- *Lobation of petal.*—Shallow.
- *Diameter.*—Approximatley 2.7–2.9 cm.
- *Color.*—Petal: Vivid reddish-purple (R.H.S. 74A, J.H.S. 9207). Base color of corolla throat: Bright greenish-yellow (R.H.S. 3A, J.H.S. 2905).
- *Outside color of corolla tube.*—Pale yellow-green (R.H.S. 1D, J.H.S. 3102).
- *Reproductive organs.*—1 normal pistil and 5 normal stamens.
- *Fertility.*—Fertile, but self-incompatible.
- *Peduncle.*—Approximately 0.7–0.8 mm in thickness, and approximately 1.8 cm in length.
- *Physiological and ecological characteristics.*—High resistance to heat, rain, drought and diseases, such as powdery mildew. The resistance to heat and rain is very strong.
- *Blooming.*—A bloom commonly lasts approximately 10 days on the plant.

Pinching is not necessary to ensure continuous blooming; however, it does tend to enhance bloom production.

SUMMARY OF THE VARIETY

This new variety of Petunia plant 'Sunbelrikupi' has a decumbent growth habit with abundant branching, and forms single small vivid reddish-purple flowers in a great profusion of blooms with the entire plant remaining in bloom for a considerable period of time. The plant has high tolerances to cold and heat, high resistance to pests and diseases, particularly powdery mildew, and high resistance to rain.

The plants described and depicted herein were propagated by the use of cuttings and were approximately eight months of age. Such cuttings were placed in a greenhouse in January, were transplanted in February, were further transplanted to pots in April and were thereafter placed outdoors. When present in a greenhouse, the plants were grown under controlled greenhouse conditions under full sunshine with no shielding from light. The minimum greenhouse temperature was maintained above 13° C.

BRIEF DESCRIPTION OF THE PHOTOGRAPHS

The depicted plants had been reproduced by the use of cuttings and were photographed during August while growing outdoors in pots at an age of approximately eight months at Youkaichi-shi, Shiga-ken, Japan.

DESCRIPTION OF THE NEW VARIETY

The botanical characteristics of the new and distinct variety of Petunia plant named 'Sunbelrikupi' are as follows when observed during August at Youkaichi-shi, Shiga-ken, Japan:

Plant:

*Growth habit.*—Decumbent.

*Plant height.*—Approximately 7.0 cm.

*Spreading area of plant.*—The stem extends to a length of 18 cm from the base.

*Blooming period.*—April to late October in the southern Kanto area, Japan. The plant shape does not change throughout this period.

Stem:

*Thickness.*—Approximately 1.5 mm.

*Pubescence.*—Sparse.

*Branching.*—Extremely abundant with a superior branching propensity, especially with respect to secondary branches.

*Length of internode.*—Approximately 1.8 cm.

Leaf:

*Shape.*—Lanceolate.

*Length.*—Approximately 3.2 cm.

*Width.*—Approximately 1.3 cm.

*Color.*—Moderate olive-green (R.H.S. 147A, J.H.S. 3509) on the upper surface and R.H.S. 137C on the under surface.

*Venation.*—Pinnate and generally of the same coloration as the remainder of the leaves.

*Texture.*—Smooth.

*Margin.*—Entire.

*Thickness.*—0.5 mm.

*Pubescence.*—Sparse.

*Leaf attachment angle to stem.*—Substantially horizontal.

Flower:

*Facing direction.*—Slanted upward.

*Type.*—Single.

*Shape.*—Funnel-shaped, with five fissures.

*Shape of petal tip.*—Round.

*Waviness of petal.*—Weak.

*Lobation of petal.*—Shallow.

*Diameter.*—Approximately 3.5 cm.

*Color.*—Petal: Vivid reddish-purple (R.H.S. 74A, J.H.S. 9207). The base color of corolla throat: Brilliant greenish-yellow (R.H.S. 8A, J.H.S. 2704).

*Outside color of corolla tube.*—Light greenish-yellow (R.H.S. 5C, J.H.S. 2904).

Figure 1:
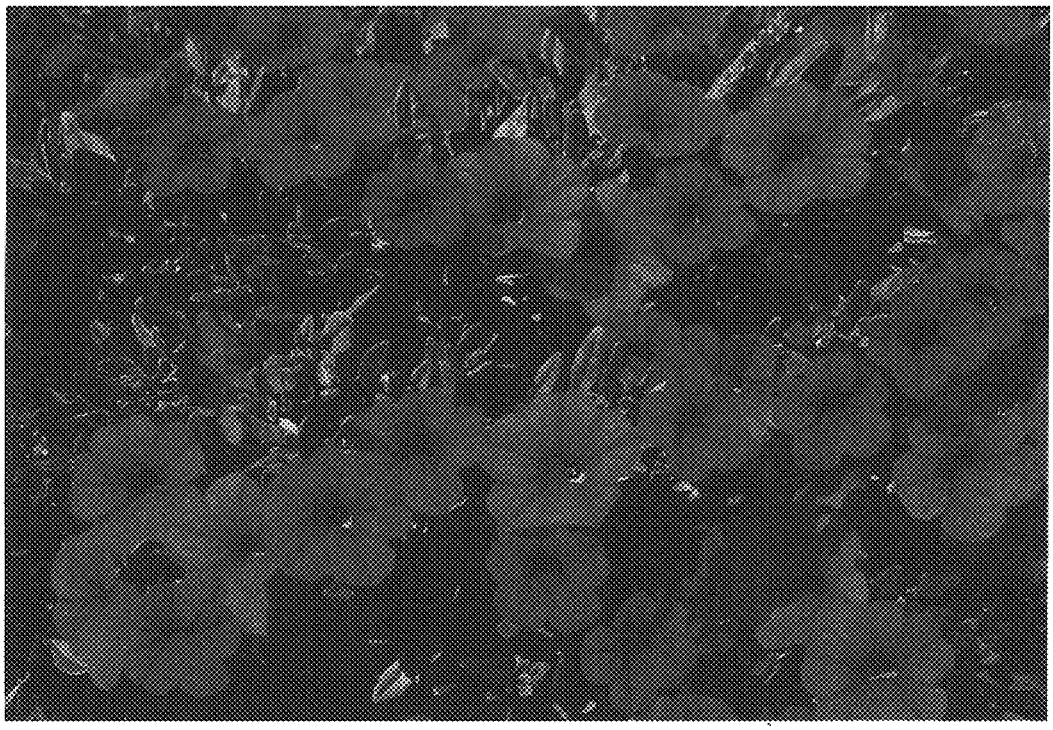
FIG. 1 is a photograph of flowers and leaves of the new variety of Petunia plant 'Sunbelrikupi'.
Figure 2:
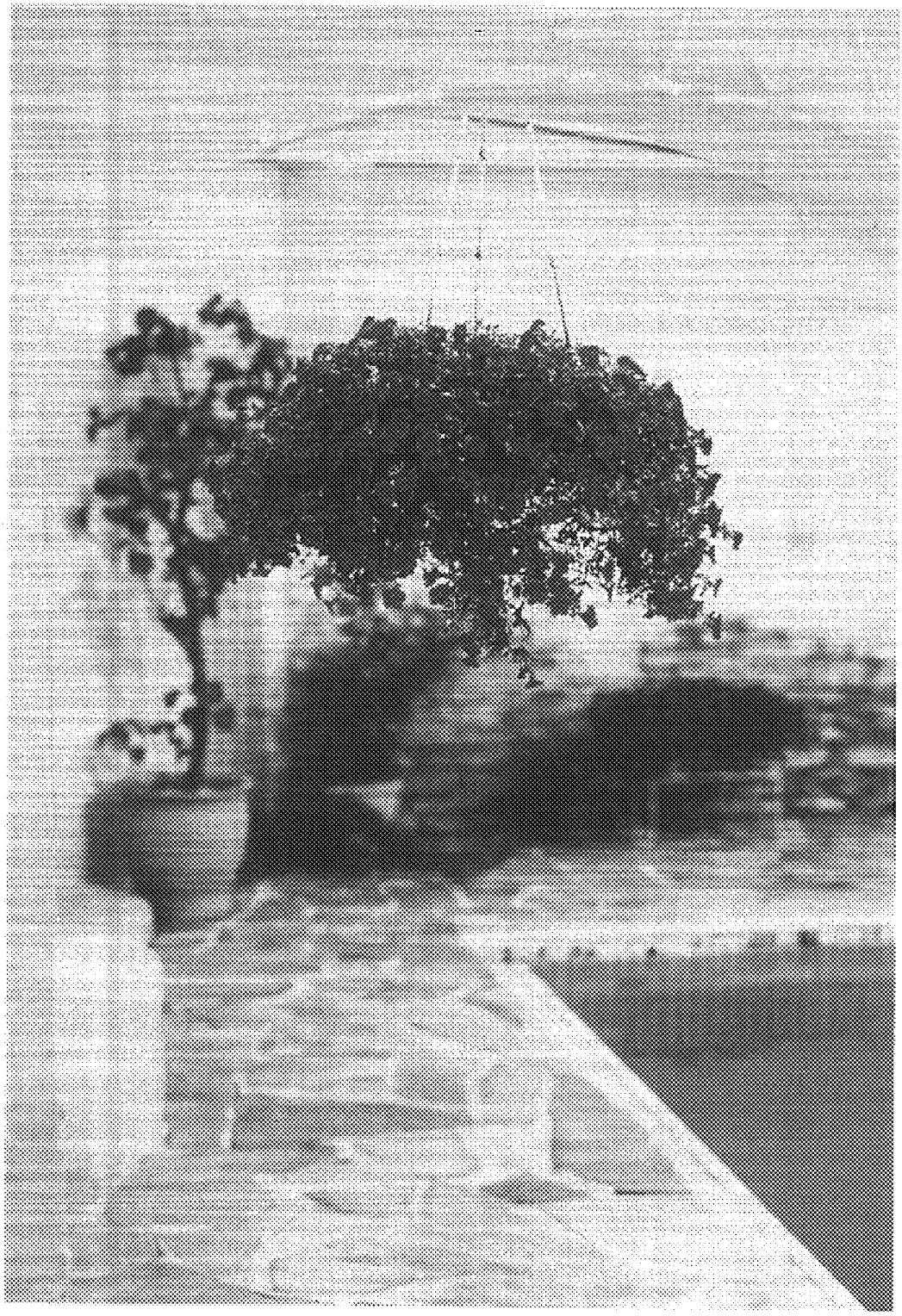
FIG. 2 is a photograph of an entire plant of the new variety of Petunia plant 'Sunbelrikupi' while growing in a hanging pot.

*Venation.*—R.H.S. 59B in coloration, main veins generally radiate linearly outwardly from the center with much fine branching as illustrated in FIG. 1.

*Sepals.*—R.H.S. 144A on the upper and lower surfaces, generally lanceolate in configuration, with an entire margin, approximately 13.5 mm in length, approximately 3 mm in width at the widest point, and five in number. The calyx is tubular and divides into five sepals.

*Reproductive organs.*—1 normal pistil and 5 normal stamens. The stigma is club-shaped and R.H.S. 145A in coloration. The style is approximately 7 mm in length and R.H.S. 145D in coloration. The ovary is R.H.S. 145A in coloration. The stamens commonly are of variable lengths from approximately 5.1 to 7.7 mm. Pollen is formed in a quantity that is typical of *Petuna hybrida* and is near R.H.S. 17A in coloration.

*Fertility.*—Fertile, but self-incompatible.

*Peduncle.*—Approximately 0.9 mm in thickness, and approximately 3.4 cm in length. R.H.S. 177A on the upper side and R.H.S. 144B on the lower side. The texture is smooth.

*Seeds.*—R.H.S. N186A in coloration, approximately 0.6 mm in diameter, and generally round. The quantity is typical of *Petunia hybrida.*

*Physiological and ecological characteristics.*—High resistance to heat, rain, drought and diseases, such as powdery mildew. The resistance to heat and rain is very strong.

*Blooming.*—A bloom commonly lasts approximately 10 days on the plant. Pinching is not necessary to ensure continuous blooming; however, it does tend to enhance bloom production.

This new variety of Petunia plant is most suitable for flower bedding and potting, particularly in hanging pots or in planters, and is excellent for use as a ground cover. Pinching of old blossoms will enhance the formation of new blossoms.

I claim:

1. A new and distinct variety of Petunia plant, substantially as herein illustrated and described, characterized particularly as to novelty by (A) having a decumbent growth habit, (B) great profusion of blooms with the entire plant remaining in bloom for a considerable period of time, (C) flowers are single and small with petals having a vivid reddish-purple color, and (D) a high resistance to rain, heat, drought and disease.

* * * * *